United States Patent [19]
Griffin et al.

[11] Patent Number: 6,156,739
[45] Date of Patent: Dec. 5, 2000

[54] QUINAZOLINONE COMPOUNDS

[75] Inventors: Roger John Griffin, Northumberland; Alan Hilary Calvert; Jane Nicola Curtin, both of Tyne & Wear; David Richard Newell, Northumberland; Bernard Thomas Golding, Newcastle upon Tyne, all of United Kingdom

[73] Assignee: Newcastle University Ventures Limited, Newcastle Upon Tyne, United Kingdom

[21] Appl. No.: 09/362,901

[22] Filed: Jul. 29, 1999

Related U.S. Application Data

[63] Continuation of application No. PCT/GB98/00303, Jan. 30, 1998.

[30] Foreign Application Priority Data

Feb. 1, 1997 [GB] United Kingdom .................. 9702701

[51] Int. Cl.[7] .................. A01N 57/00; A61K 31/675; C07F 9/02
[52] U.S. Cl. .................. 514/80; 514/80; 544/244
[58] Field of Search ................. 514/80; 544/244

[56] References Cited

U.S. PATENT DOCUMENTS 5,798,344  8/1998  Kuroki et al. ..................... 514/80

FOREIGN PATENT DOCUMENTS 0 749 974  12/1996  European Pat. Off. ...... C07F 9/6512
95/24379    9/1995  WIPO ......................... C07C 235/46
WO 95/24379 9/1995  WIPO .

*Primary Examiner*—Mukund J. Shah
*Assistant Examiner*—Ben Schroeder
*Attorney, Agent, or Firm*—Pillsbury Madison & Sutro LLP

[57] ABSTRACT

Phosphate derivatives are disclosed of quinazolinone compounds having structural formula (I) or a pharmaceutically acceptable salt thereof, wherein X' represent hydroxyl, alkyl, alkoxy, or O—Z where Z is a phosphate or phosphate derivative; Y' represents hydrogen, alkyl or an optionally substituted aryl group or optionally substituted aralkyl group; and R' is hydrogen, alkyl, or $CH_2$—O—Z where Z is again a phosphate or phosphate derivative; subject to the proviso that if neither X' nor R' contains Z, Y' is an aryl or aralkyl group having an O—Z substituent therein with Z once again being a phosphate or phosphate derivative as hereinabove defined. These compounds are useful as pro-drugs for providing active PARP inhibiting substances for medical use in conjunction with a cytotoxic drug or radiotherapy in order to increase the effectiveness of the latter, especially in connection with antitumor treatment.

(I)

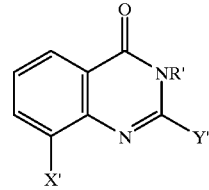

19 Claims, No Drawings

QUINAZOLINONE COMPOUNDS

This is a continuation of International Appln. No. PCT/GB98/00303 filed Jan. 30, 1998.

The present invention relates to certain quinazolinone compounds that are of interest for use as chemotherapeutic agents, especially quinazolinone compounds that have an ability to inhibit the activity of the enzyme poly ADP-ribosyltransferase (EC 2.4.2.30), also known as poly(ADP-ribose)polymerase, commonly referred to as ADPRT or PARP. In general, the latter abbreviation, PARP, will be used throughout the present specification.

Many quinazolinone compounds are known to have useful chemotherapeutic properties and there has been disclosed in our PCT international patent specification No. WO 95/24379 a particular group of quinazolinone compounds showing PARP inhibitory activity that have the general structural formula I'

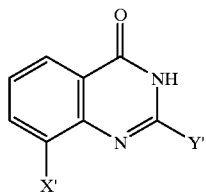

wherein, inter alia,

X' represents hydroxyl, alkyl or alkoxy, and

Y' represents hydrogen, alkyl or an optionally substituted aryl (e.g. phenyl) or aralkyl (e.g. benzyl) group.

The above-mentioned quinazolinone compounds have been considered to be of interest as promising therapeutic agents for use in conjunction with cytotoxic drugs or radiotherapy, for example in antitumour treatment, because their PARP inhibiting activity can enable them to interfere with intracellular DNA repair mechanisms and thereby potentiate or enhance the effectiveness of such cytotoxic drugs in chemotherapy, or of radiation in radiotherapy. However, a serious practical limitation in many cases has been the limited solubility of the compounds in pharmaceutically acceptable solvents.

The present invention has developed from efforts to produce analogues or derivatives of these quinazolinone compounds having greater aqueous solubility, more suitable for use in pharmaceutical formulations, and capable of acting as prodrugs which will biologically degrade or break down in vivo to release the active compound within the body after being administered to a patient in need of treatment.

The term "prodrug" is used in the present specification to denote modified forms or derivatives of a pharmacologically active compound which biodegrace in vivo and become converted into said active compound after administration, especially but not exclusively oral or intravenous administration, in the course of therapeutic treatment of a mammal. Such prodrugs are commonly chosen because of an enhanced solubility and/or stability in aqueous media which helps to overcome formulation problems, and also in some cases to give a relatively slow or controlled release of the active agent.

With some other pharmaceutical compounds successful water-soluble prodrug forms have been made by incorporating a carbamate ester. However, attempts to produce successful prodrug forms of these quinazolinone compounds by likewise incorporating a carbamate ester group have been unsuccessful because although it has been possible in some cases to convert a hydroxyl substituent in the quinazolinone ring system into a carbamate ester, the product has been found to be too unstable for clinical use. For example, in preliminary experiments the compound 8-hydroxy-2-methylquinazolin-4-[3 H]-one was converted into glycine carbamate ethyl ester using 1.1 mol. equivalents of ethyl isocyanatoacetate in the presence of 2 mol. equivalents of triethylamine. The reaction was found to be high yielding and clean, with a simple recrystallisation giving the desired product. However, when submitted for biological testing, the carbamate ester produced was found to be only moderately active against PARP and less active than the starting compound. Deprotection to remove the ethyl group and produce the target glycine carbamate was then carried out using a 1:1 ratio of THF and 0.5 M aqueous $H_2SO_4$. Although promising $^1$H NMR data were obtained for the deprotected product and the compound was found to dissolve readily in aqueous sodium bicarbonate solution, indicating that it easily formed the requisite sodium salt, further $^1$H NMR studies demonstrated that after dissolution in sodium bicarbonate solution the compound decomposed back to the starting material, as opposed to forming a stable salt. Thus, the carbamate ester was unstable towards alkaline hydrolysis. Numerous subsequent investigations into the stability of carbamate esters towards alkaline hydrolysis have confirmed that at least for the purpose of producing a water-soluble quinazolinone which will enzymatically biodegrade, especially in plasma, this pH dependence and alkaline instability renders such carbamate esters unsuitable for clinical use.

It has, however, now been discovered that satisfactory prodrug forms of these quinazolinone compounds can be produced in the form of phosphates or phosphate derivatives (including salts thereof)

More specifically, from one aspect the present invention provides compounds for use in therapy having the general structural formula I

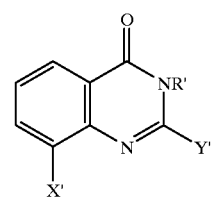

and pharmaceutically acceptable salts thereof, wherein

X' represents hydroxyl, alkyl, alkoxy or O—Z where Z is a phosphate or phosphate derivative;

Y' represents hydrogen, alkyl or an optionally substituted aryl group or optionally substituted aralkyl group; and R' is hydrogen, alkyl, or $CH_2$—O—Z where Z is again a phosphate or phosphate derivative;

subject to the proviso that if neither X' nor R' contains Z, Y' is an aryl or aralkyl group having an O—Z substituent therein with Z as before being a phosphate or phosphate derivative as defined above.

The term "optionally substituted" means that the aromatic ring of the aryl group (e.g. phenyl or napthyl) or aralkyl group (e.g. phenylalkyl or benzyl) group concerned may be unsubstituted or may have at least one substituent.

Alkyl groups when present as such or as a moiety in other groups will generally be straight-chain or branched-chain or cyclic alkyl groups composed of 1–6 carbon atoms, and more usually 1–4 carbon atoms. In particular, when either X' or Y' is, or includes, an alkyl or an alkoxy group this will generally be $C_{1-6}$ alkyl or alkoxy, such as for example methyl, ethyl, n-propyl, i-propyl, n-butyl, t-butyl, cyclohexyl, or methoxy, ethoxy, etc.

If R' is alkyl, it is preferably methyl. When Y' is or includes a phenyl group this may be substituted, for instance in the 4 (para) position but alternatively, or additionally, in the 2-position and/or 3-position, by various substituents as hereinafter mentioned.

Thus, preferred compounds of structural formula I include compounds in which Y' is phenyl or benzyl having at least one substituent in the benzene ring selected from hydroxy, alkoxy, $NO_2$, $N_3$, $NR_5R_6$ ($R_5$ and $R_6$ each being independently hydrogen or alkyl), $NHCOR_3$ ($R_3$ being alkyl or aryl), $CO_2R_4$ ($R_4$ being H or alkyl), an amide $CONR_8R_9$ ($R_8$ and $R_9$ each being independently hydrogen or alkyl), tetrazoyl, alkyl, hydroxyalkyl or a phosdhorylated hydroxyalkyl, $CW_3$ or W (W being halogen), CN, and O—Z.

More particularly, where Y' represents a substituted phenyl group having the structural formula II

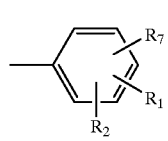

II $R_1$, $R_2$ and $R_7$ may be each selected independently from H, hydroxy, alkoxy, $NO_2$, $N_3$, $NR_5R_6$ ($R_5$ and $R_6$ each being independently hydrogen or alkyl), $NHCOR_3$ ($R_3$ being alkyl or aryl), $CO_2R_4$ ($R_4$ being H or alkyl), an amide $CONR_8R_9$ ($R_8$ and $R_9$ each being independently hydrogen or alkyl), tetrazoyl, alkyl, hydroxyalkyl or a phosphorylated hydroxyalkyl, $CW_3$ or W (W being halogen), CN, and O—Z.

Compounds of particular interest include compounds as specified above where Y' represents a substituted phenyl group having the structural formula II with one of $R_1$, $R_2$ and $R_7$ being a 4'-CN, 4'-$CO_2H$, a 4'-tetrazole or a 3'-$OPO_3^-$ or 4'-$OPO_3^-$ substituent and the others being hydrogen.

The invention also embraces or extends in some cases to quinazolinone compounds which are intermediates in the preparation of, or precursors of, the phosphate compounds disclosed herein wherein such quinazolinone compounds are novel chemical compounds. These include quinazolinone compounds conforming to structural formula I (or I') in which X' is OH and Y' conforms to structural formula II with one of $R_1$, $R_2$ and $R_7$ being 4'-CN, 4'-$NH_2$, 4'-$CO_2Me$, 4'-COOH; 4'-OH, 4'-$CF_3$, 4'-$CONH_2$ or 4'-tetrazole.

Compounds of structural formula I or I', as hereinabove defined with or without the phosphate grouping O—Z and in which Y' is an aromatic ring that includes a CN substituent, may also often be particularly useful as intermediates in making other compounds in accordance with the invention because a cyano substituent can usually be converted, using standard methodology, into a variety of other functional groups, including amine, carboxyl, amide and tetrazole for example.

It will be understood that phosphate compounds in accordance with the present invention may also include diphosphorylated compounds in which substituents X' and Y' at the 8 and 2 positions both include a phosphate group. Also, although the phosphates will usually be phosphate monesters, they may also be phosphate diesters, e.g. monobenzyl phosphate derivatives. Phosphate triesters are not expected to act as satisfactory prodrugs in themselves, but can nevertheless constitute useful intermediates for preparing phosphate monoesters or diesters as hereinafter described.

The phosphate compounds of the invention will generally be prepared by phosphorylating the hydroxyl group(s) of a corresponding hydroxyquinazolinone. In preferred embodiments the phosphorylation is arranged to provide, in the first instance, a dibenzyl phosphate ester from which one or both benzyl groups may be selectively removed as required. Thus, from another aspect the invention also includes a process for preparing a phosphate prodrug modification of a quinazolinone as defined above wherein the quinazolinone starting material having a hydroxyl substituent, preferably but not necessarily at position 8, is treated with a phosphorylating agent, e.g. with a dibenzyl phosphonate such as dibenzyl chlorophosphonate in the presence of a base, e.g. N,N-diisopropylethylamine, to provide a dibenzyl phosphate ester, followed by removal of one or both of the benzyl groups.

In an initial attempt to prepare a phosphate prodrug modification, the previously mentioned compound 8-hydroxy-2-methylquinazolin-4-[3 H]-one was treated with 1.1 mol equivalents of diphenyl chlorophosphate in the presence of N,N-diisopropylethylamine, using dry acetonitrile as solvent, to produce the diphenyl protected phosphate ester. This first stage reaction was found to be clean and high yielding, and satisfactory analytical results were obtained for the product. In the next stage, deprotection of the diphenyl phosphate ester was attempted using a Parr hydrogenation procedure at 45–50 psi (310–345 kPa). The diphenyl phosphate ester and platinum oxide (Adam's catalyst), in ethanol, were hydrogenated for 4 hours, in an attempt to produce the phosphate. However, it was found that under these conditions the parent quinazolinone could be detected, indicating that the phosphate group had been cleaved during hydrogenation. Also, a small quantity of 2-methylquinazolin-4-[3 H]-one was evident, and the product isolated gave unsatisfactory $^1H$ NMR data.

It was then discovered, however, that more satisfactory results could be obtained by first preparing a dibenzyl phosphate ester because, surprisingly, it has proved possible to remove the benzyl groups by hydrogenation more easily than corresponding phenyl groups in order to give the required phosphate derivative.

Thus, in one example of preparing a phosphate prodrug, 8-(O-phosphoryl)-2-methylquinazolin-4-[3 H]-one, of which a more detailed description is given later, the dibenzyl phosphate ester thereof was synthesised by treating the compound 8-hydroxy-2-methylquinazolin-4-[3 H]-one with dibenzyl chlorophosphonate, in the presence of N,N-diisopropylethylamine. The dibenzyl chlorophosphonate for this purpose was made in situ by treating dibenzyl phosphite with N-chlorosuccinimide, followed by separation of the succinimide by-product from the reaction mixture. The dibenzyl chlorophosphonate thus obtained was then used as a solution in acetonitrile for the subsequent phosphorylation of the quinazolinone compound.

In another, alternative, method of preparing the dibenzyl phosphate ester referred to above, the compound 8-hydroxy-2-methylquinazolin-4-[3 H]-one was treated with carbon tetrachloride (5 equivalents) in dry acetonitrile at −10° C. together with a mixture of primary/secondary mines, namely N,N-diisopropylethylamine (2.1 equivalents) and N,N-dimethylaminopyridine (0.1 equivalents), and dibenzyl phosphite (1.45 equivalents). This alternative method can be particularly convenient, involving a mild and clean reaction that may be complete within an hour with quite satisfactory yields.

Removal of the benzyl groups of the dibenzyl phosphate ester to give the free phosphate was effected using a 1:1 mixture of THF (redistilled from sodium/benzophenone, then from LiAlH$_4$) and water as solvent. Hydrogenation was carried out under ambient temperature and pressure, using 10% palladium on carbon catalyst. On completion of the reaction, a white precipitate formed which was redissolved in an excess of water in order to remove the catalyst by filtration.

The product obtained was readily soluble in aqueous sodium bicarbonate solution giving the disodium salt, and preliminary results from HPLC studies have been extremely promising, indicating that the compound produced is stable in aqueous solution over several days at least. It was also found that the product undergoes a facile plasma-mediated conversion back to the parent quinazolinone and this conversion is indeed enzyme-dependent and not pH-dependent, unlike the carbamate ester.

If it is desired to prepare the corresponding monobenzyl substituted phosphate ester, this can be conveniently carried out by first preparing the dibenzyl phosphate ester as described above and then carrying out a controlled hydrogenation so as to give a reasonably good yield of product in which only one benzyl group is removed. This may then be further purified as required.

The overall reactions involved in forming the dibenzyl phosphate ester and the subsequent selective removal of the benzyl groups and production of corresponding sodium phosphate salts can be depicted as follows:

As will be appreciated, phosphate derivatives of other quinazolinone compounds having a hydroxyl group amenable to phosphorylation may be prepared in a similar manner to provide prodrug forms in accordance with the invention.

It should also be understood that where any of the compounds referred to can exist in more than one enantiomeric form, all such forms, mixtures thereof, and their preparation and uses are within the scope of the invention.

The phosphate prodrug compounds of the present invention will usually be used in the form of water-soluble ammonium or alkali metal phosphate salts. A few further examples of sodium phosphate salts of such compounds, including a compound in which Y' is a phenyl group having a phosphate group as a 3'-substituent, and including also a diphosphorylated compound, are illustrated in the diagram below. These can all be prepared from the corresponding quinazolinone hydroxy derivatives.

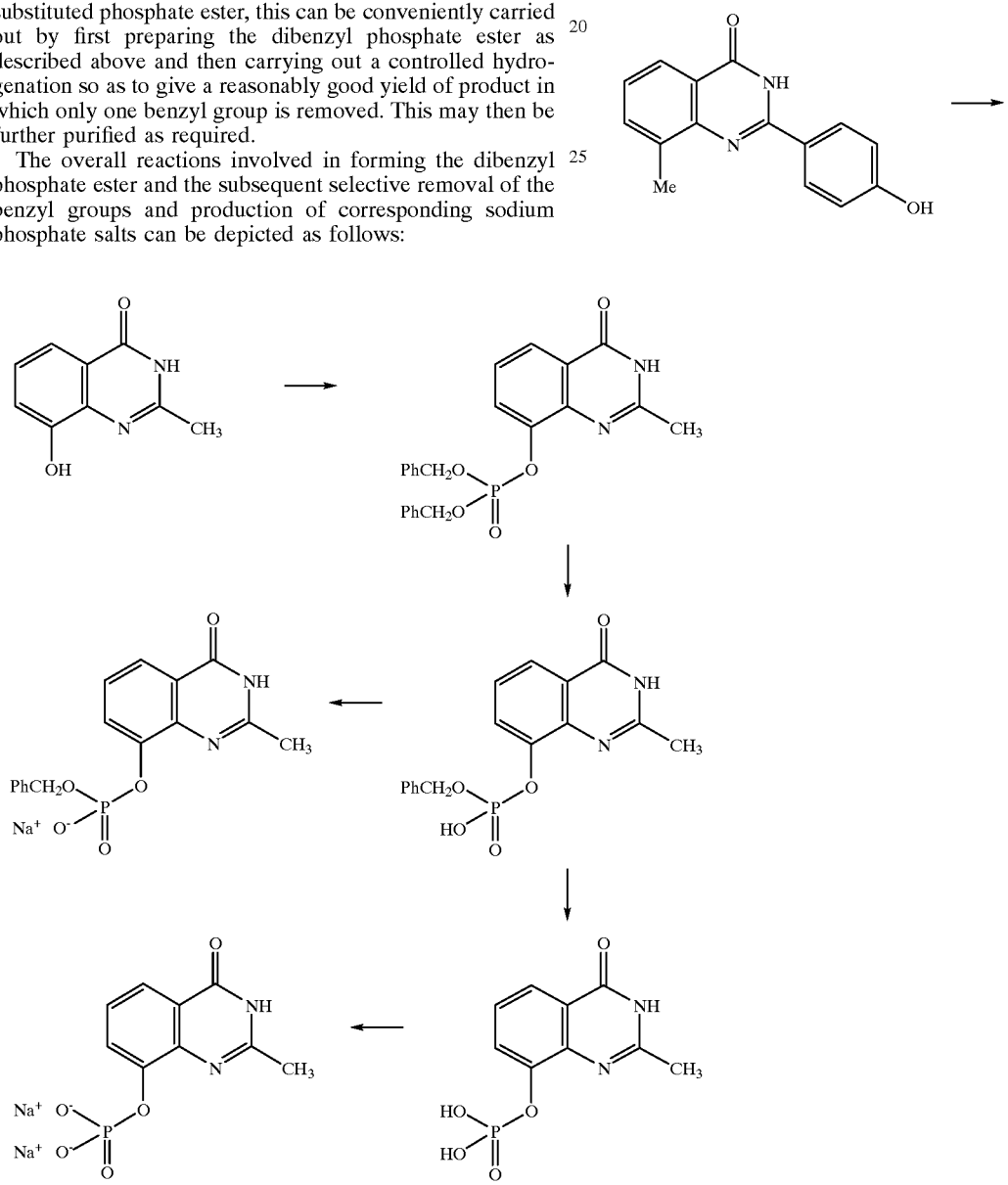

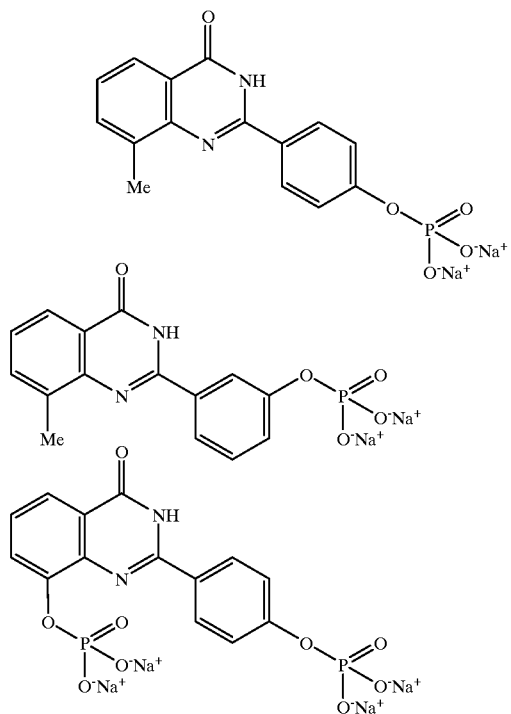

Compounds in accordance with the invention in which R' is a phosphate, in particular compounds that are phosphate esters of 3-(hydroxymethyl)-quinazolinone, may be prepared from the appropriate quinazolinone using a method substantially as described by Varia et al. (1984) *J. Pharm. Sci.* 73, 1068. This will involve treatment of the appropriate quinazolinone with 37% aqueous formaldehyde, in the presence of potassium carbonate, to give a N-hydroxymethyl derivative, which can be converted to the corresponding N-chloromethylquinazolinone. Phosphorylation with silver dibenzylphosphate, and removal of the benzyl groups by catalytic hydrogenation, will then afford the required phosphate prodrug, which can be readily converted to the water-soluble disodium salt by conventional methods.

The reactions concerned in preparing N-hydroxymethyl phosphate esters of quinazolinones as outlined above in order to provide water-soluble prodrugs are illustrated in the diagram below.

In an alternative method the quinazolinone starting material could be reacted directly with dibenzyl chloromethylphosphate [PO(BnO)$_2$OCH$_2$Cl] to furnish the dibenzyl phosphate, subsequent hydrogenation then giving the required phosphate derivative as before.

Prodrugs of this type combine excellent acueous solubility with a facile conversion to the parent drug in vivo.

It will be understood that the invention expends also to the therapeutic use of the phosphate prodrug compounds herein disclosed, including their use for making medical or veterinary preparations or pharmaceutical formulations comprising compositions containing an effective PARP inhibitory amount of the active compound for administration to a patient in conjunction with a cytotoxic drug or radiotherapy in order to increase the cytotoxic effectiveness of the latter.

Such preparations or formulations may be made up in accordance with any of the methods well known in the art of pharmacy for administration in any suitable manner, for example orally, parenterally (including subcutaneously, intramuscularly or intravenously), or topically, the mode of administration, type of preparation or formulation and the dosage being generally determined by the details of the associated cytotoxic drug chemotherapy or radiotherapy that is to be enhanced.

In making up such pharmaceutical formulations in the form of sterile liquid preparations for parental use for instance, a predetermined therapeutically effective non-toxic amount of the particular compound concerned may be dissolved in phosphate buffered saline and the preparations may be presented in unit dosage form contained in sealed ampoules ready for use. In general, at least in aqueous solution, concentrations not greater than 200 mg/ml will be preferred, but the amount and dosage routine required for optimum effectiveness will of course vary and is ultimately at the discretion of the medical or veterinary practitioner treating the mammal in each particular case. Where the compound is to be used in conjunction with a cytotoxic drug, the latter in some cases may be administered simultaneously and may conveniently be incorporated in the same pharmaceutical formulation or composition.

DETAILED DESCRIPTION OF SPECIFIC EMBODIMENTS

The following examples and descriptions of stages in synthetic routes of preparation of various preferred compounds of interest serve to further illustrate the present

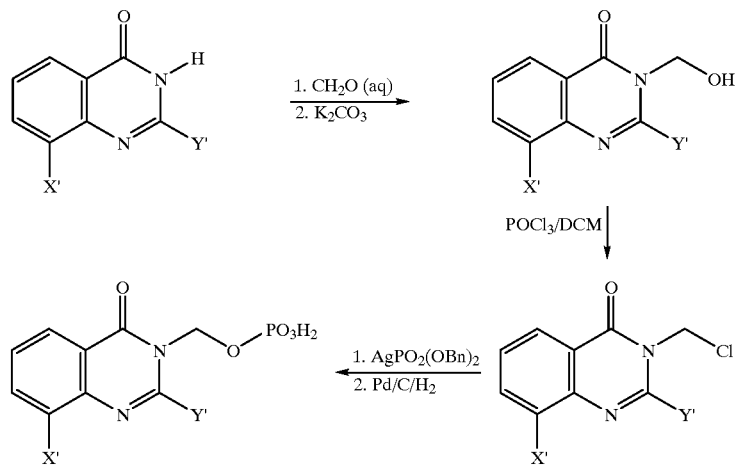

invention, but should not be construed in any way as a limitation thereof.

In the first example (EXAMPLE 1), more detailed description is given of stages in a synthetic route of preparation of the previously mentioned specific quinazolinone phosphate prodrug compound 8-(O-phosphoryl)-2-methylquinazolin-4-[3 H]-one, representing by way of example one particular preferred compound of interest. As will be seen, in the first stages of the synthetic process the preparation is described of various intermediate compounds required for the preparation of the final prodrug product.

EXAMPLE 1

8-(O-phosphoryl)-2-methylquinazolin-4-[3 H]-one (a) 1st Stage—Preparation of 3-Methoxy-2-nitrobenzamide 3-Methoxy-2-nitrobenzoic acid (3.0 g, 15.2 mmol) was dissolved in dry THF (50 ml). Thionyl chloride (1.7 ml, 22.8 mmol) was added, with 2 drops of DMF and the reaction mixture was stirred for 12 hours, under nitrogen at room temperature. The reaction mixture was added dropwise to an excess of aqueous ammonia solution (18 ml) and a cream precipitate formed. After 15 minutes, the solvent was removed under vacuum and the remaining slurry was washed with ice-cold water and collected by filtration (2.88 g, 14.7 mmol, 97%), m.p. 219–222° C.; Found C 49.03, H 3.93, N 13.97, $C_8H_8N_2O_4$ requires C 48.98. H 4.11, N 14.28%.

(b) 2nd Stage—Preparation of 3-Methoxy-2-aminobenzamide

3-Methoxy-2-nitrobenzamide (1.4 g, 7.1 mmol) was dissolved in dry methanol (80 ml) with palladium-carbon catalyst (150 mg) and the reaction vessel was placed under an atmosphere of hydrogen at ambient temperature and pressure until no further hydrogen absorption was observed. The catalyst was removed by filtration through Celite™ to leave a colourless solution. The solvent was removed under vacuum to afford the title compound in excellent yield (1.17 g, 7.0 mmol, 99%), m.p. 145–147° C.; Found C 57.54, H 5.99, N 16.61, $C_8H_{10}N_2O_2$ requires C 57.82, H 6.07, N 16.86%.

(c) 3rd Stage—Preparation of 8-Methoxy-2-methylquinazolin-4-[3 H]-one

3-Methoxy-2-aminobenzamide (1.5 g, 9.0 mol) was dissolved in dry THF (35 ml) with dry pyridine (0.95 ml, 11.7 mmol). Acetyl chloride (1.4 ml, 19.9 mmol) was dissolved in dry THF (2 ml), added dropwise to the reaction mixture and stirred for 12 hours under nitrogen, at room temperature. The solvent was removed under vacuum and the remaining white slurry was resuspended in 2% aq. NaOH solution and neutralised with 1.0 M HCl. The resulting white precipitate was collected by filtration and recrystallised from methanol/water (1.67 g, 8.8 mmol, 97% yield), m.p. 202–204° C. (sublimation); Found C 62.14, H 5.18, 5.29, N 14.23, 14.36, $C_{10}H_{10}N_2O_2$. 0.1 mol $H_2O$ requires C 62.55, H 5.25, N 14.59%.

(d) 4th Stage—Preparation of 8-Hydroxy-2-methylquinazolin-4-[3 H]-one

8-Methoxy-2-methylquinazolin-4-[3 H]-one (0.7 g, 3.7 mmol) was dissolved in a 1.0 M solution of $BBr_3$ in DCM (8.4 ml, 8.4 mmol), and gently refluxed for 24 hours under nitrogen. The alkyl bromide was directly distilled from the reaction mixture and the remaining residue was hydrolysed with 10% aq. NaOH solution (clear, off-white solution), then acidified with 1.0 M HCl. The resulting precipitate was collected and the filtrate was extracted with 3×30 ml EtOAc, dried (MgSO$_4$), filtered and the solvent was removed under vacuum. The title compound was recrystallised from propan-2-ol/water (0.42 g, 2.4 mmol, 65% yield), m.p. 253–258° C.; Found C 61.39, H 4.54, N 15.88, $C_9H_8N_2O_2$ requires C 61.36, H 4.58, N 15.91%.

(e) 5th Stage—Preparation of Dibenzyl chlorophosphonate

Dibenzyl phosphite (0.5 ml, 2.3 mmol) was dissolved in dry acetonitrile (10 ml). N-Chlorosuccinimide (0.23 g,mmol) was added, whereupon a fine white precipitate rapidly formed. After stirring at room temperature for 2 hours under nitrogen the reaction mixture was filtered, to give a clear solution of the title compound in dry acetonitrile.

(f) 6th Stage—Preparation of 8-(O-dibenzyl phosphoryl)-2-methylquinazolin-4-[3 H]-one Method 1

8-Hydroxy-2-methylquinazolin-4-[3 H]-one (0.5 g, 2.8 mmol) was suspended in dry acetonitrile (20 ml) with N,N-diisopropylethylamine (1 ml, 5.6 mmol). A solution of dibenzyl chlorophosphonate in acetonitrile (1.7 g in 22.2 ml) was slowly added dropwise and the reaction mixture was stirred under nitrogen for 48 hours. Further equivalents of dibenzyl chlorophosphonate and N,N-diisopropylethylamine were added until TLC showed no starting material present. Isopropanol (5 ml) was added and the solvents were removed under vacuum to leave a pink oil. The oil was redissolved in DCM and washed with water. The organic layer was dried (MgSO$_4$), filtered and the solvent was removed under vacuum to give a dark pink oil which was recrystallised from aq. methanol (0.35 g, 0.8 mmol, 28%), m.p. 134–135° C.; $U_{max}$/cm$^{-1}$ 3168, 3091, 3043, 2964, 2896, 2803, 1688; $\delta_H$ (200 Mhz, d$_6$-DMSO) 2.41 (s, 3 H, —CH$_3$), 5.40 (s, 2 H, —CH$_2$Ph), 5.44 (s, 2 H, —CH$_2$Ph), 7.47–7.56 (m, 11 H, Ar-6 H and 2×Ph-2'/3'/4'/5'/6' H), 7.67–7.73 (m, 1 H, Ar-7 H), 8.01–8.05 (m, 1 H, Ar-5 H), 12.5 (br s, 1 H, —NH); m/z (FAB) 437 (MH$^+$, 70%), 421 ([M—O]$^+$), 107 (OBn$^+$), 91 (Bn$^+$).

Alternative Method 2

8-hydroxy-2-methylquinazolin-4-[3 H]-one (0.2 g, 1.1 mmol) was placed in a three-necked flask which was fitted with septa, a thermometer and nitrogen inlet. Dry acetonitrile (25 ml) was added and the mixture was cooled to −10° C. Carbon tetrachloride (0.54 ml, 5.5 mmol) was added and the solution stirred. N,N-diisopropyl-ethylamine (0.42 ml, 2.4 mmol) followed by N,N-dimethyl-aminopyridine (0.014 g, 1.1 mmol) were added. One minute later, dropwise addition of dibenzyl phosphite (0.36 ml, 1. 6 mmol) was begun. Care was taken to ensure the internal temperature of the reaction mixture did not rise above −10° C. On completion of the reaction (as determined by TLC, after 1 hour), 0.5 M aq. potassium dihydrogen orthophosphate solution (32 ml/100 ml acetonitrile) was added and the mixture was allowed to warm to room temperature. The mixture was extracted three times with EtOAc. The combined EtOAc layers were washed with water then saturated brine solution. The organic layers were dried (Na$_2$SO$_4$) and the solvent was removed under vacuum to give a white "oily" solid. The product was purified by column chromatography, using (6:4) DCM:acetonitrile as the eluent, (0.24 g, 0.5 mmol, 49%). The product was found to be identical by TLC to the product synthesised by Method 1.

(g) Final Stage—Preparation of 8-(O-phosphoryl)-2-methylquinazolin-4-[3 H]-one

8-O-(dibenzylphosphoryl)-2-methylquinazolin-4-[3 H]-one (0.07 g, 0.16 mmol) was suspended in THF (5 ml, redistilled from LiAlH$_4$) and water (5 ml) with 10% palladium-carbon catalyst and the reaction vessel was placed under an atmosphere of hydrogen at ambient temperature and pressure until no further hydrogen absorption was observed. A white precipitate formed, and a further 50 ml water was added, whereby the precipitate appeared to dissolve. The reaction mixture was filtered through Celite™ to remove the catalyst. The THF and most of the water were removed under vacuum. The remaining aqueous solution was freeze-dried to give a white solid (0.03 g, 0.12 mmol, 74%), $\delta_H$ (200 (Mhz, $d_6$-DMSO) 2.46 (s, 3 H, —$CH_3$), 7.41–7.45 (t, 1 H, Ar-6 H), 7.82–7.86 (d, 1 H, Ar-7 H), 7.96 (d, 1 H, Ar-5 H).

FURTHER EXAMPLES

Examples of other quinazolinone compounds having one or more hydroxyl groups amenable to phosphorylation that may be treated in a similar manner using dibenzyl chlorophosphonate to produce a dibenzyl phosphate ester which can subsequently be selectively hydrogenated to remove one or both of the benzyl groups, as described in (f) and (g) above, thereby to produce a phosphate derivative for use as a prodrug, include:

8-Hydroxy-2-(4'-cyanophenyl)quinazolin-4-[3 H]-one

8-Hydroxy-2-(4'-hydroxyphenyl)quinazolin-4-[3 H]-one

8-Hydroxy-3-N-methyl-2-methylquinazolin-4-[3 H]-one

8-Hydroxy-2-(4'-aminophenyl)quinazolin-4-[3 H]-one

8-Hydroxy-2-(4'-trifluoromethylphenylquinazolin-4-[3 H]-one

8-Hydroxy-2-(4'-nitrophenyl)quinazolin-4-[3 H]-one

8-Hydroxy-2-phenylquinazolin-4-[3 H]-one

8-Methyl-2-(4'-hydroxyphenyl)quinazolin-4-[3 H]-one

Many of the above compounds, of which it is believed all have some potential PARP inhibitory activity, can be prepared as described in the further detailed examples below. As will be seen, in many cases the starting material can be 3-Methoxy-2-aminobenzamide.

EXAMPLE 2

8-Hydroxy-2-(4'-cyanophenyl)quinazolin-4-[3 H]-one (a) 1st Stage—Preparation of 4-Cyanobenzoyl chloride 4-Cyanobenzoic acid (1.0 g, 6.8 mmol) was suspended in thionyl chloride (5 ml) and refluxed for 2 hours. The reaction mixture was cooled and the solvent was removed under water pressure to give a cream solid, which was dried in vacuo, (1.04 g, 6.3 mmol, 92%).

(b) 2nd Stage—Preparation of 8-Methoxy-2-(4'-cyanophenyl)quinazolin-4-[3 H]-one

3-Methoxy-2-aminobenzamide (0.5 g, 3.0 mmol) was dissolved in dry THF (15 ml) with dry pyridine (0.3 ml, 3.9 mmol). 4-Cyanobenzoyl chloride (0.55 g, 3.3 mmol was dissolved in dry THF (5 ml) and added dropwise, whereupon a white precipitate formed. The reaction was left stirring under nitrogen, at room temperature for 12 hours. The solvent was removed under vacuum and the remaining white solid was resuspended in 2% aq. NaOH solution to give a clear, off-white solution, which was neutralised with 1.0 M HCl. The off-white precipitate was collected by filtration. The product (0.68 g) was purified by column chromatography, using DCM:MeOH (92:8) as the eluent to give a cream solid (0.28 g, 0.82 mmol, 27%), m.p. 306–309° C.; Found C 66.19, H 4.16, N 14.13, $C_{16}H_{11}N_3O_2$ 0.75 mol. $H_2O$ requires C 66.08, H 4.33, N 14.45%.

(c) 3rd and Final Stage—Preparation of 8-Hydroxy-2-(4'-cyanophenyl)quinazoin-4-[3 H]-one 8-Methoxy-2-(4-cyanophenyl)quinazolin-4-[3 H]-one (0.2 g, 0.72 mmol) was suspended in a 1.0 M solution of $BBr_3$ in DCM (3.6 ml) to give a brown suspension, which was refluxed for 48 hours. The solvent was directly distilled from the reaction vessel to leave a -brown solid, which was hydrolysed with 10% aq. NaOH solution to give a clear, yellow solution. The solution was neutralised with dilute HCl, whereupon a yellow precipitate formed. The reaction mixture was extracted into an excess of EtOAc. The organic layers were combined, dried ($MgSO_4$) and filtered. The solvent was removed under vacuum to leave a cream solid. The product (108 mg) was purified by column chromatography, using DCM:MeOH (95:5) as the eluent, to give a cream solid (26.4 mg, 0.1 mmol), 14%).

EXAMPLE 3

8-Hydroxy-2-(4'-hydroxyphenyl)quinazolin-4-[3 H]-one (a) 1st Stage—Preparation of 3-methoxy-2-N-(4' methoxybenzoyl)aminobenzamide 3-Methoxy-2-aminobenzamide (0.5 g, 3.0 mmol) was dissolved in dry THF (15 ml) with dry pyridine (0.3 ml, 3.9 mmol) and 4-dimethylaminopyridine (18.4 mg, 0.2 mmol) The reaction mixture (colourless solution) was cooled in an ice-bath and 4-methoxybenzoyl chloride (0.5 ml, 3.3 mmol) dissolved in dry THF (2 ml) was added dropwise whereupon a white precipitate formed. The reaction mixture was stirred at room temperature until TLC indicated no starting material present. The solvent was removed under vacuum and the remaining solid was washed with sodium bicarbonate solution and water. The product was recrystallised from aqueous methanol (0.43 g, 1.4 mmol, 47%). m.p. 179–181° C.

(b) 2nd Stage—Preparation of 8-methoxy-2-(4'-methoxyphenyl)quinazolin-4-[3 H]-one 3-Methoxy-2-N-(4' methoxybenzoyl)aminobenzamide (0.25 g, 0.8 mmol) was suspended in 10% NaOH solution (40 ml) and gently refluxed for 2 hours. The reaction mixture was neutralised with 20% aqueous HCl and a white precipitate formed which was collected by filtration and recrystallised from aq. methanol (0.15 g, 0.5 mmol, 63%), m.p. 226–228° C.

(c) 3rd and Final Stage—Preparation of 8-Hydroxy-2-(4'-hydroxyphenyl)quinazolin-4-[3 H]-one 8-Methoxy-2-(4'-methoxyphenyl)quinazolin-4-[3 H]-one (0.2 g, 0.71 mmol) was suspended in a 1.0 M solution of $BBr_3$ in DCM (2.2 ml), to give a yellow suspension, which was gently refluxed for 48 hours. The solvent was directly distilled from the reaction vessel to leave a yellow/brown solid, which was hydrolysed with 10% aq. NaOH solution to give a bright yellow, clear solution. The solution was neutralised with 1.0 M aqueous HCl whereupon a cream precipitate formed, which was collected by filtration. The filtrate was extracted into EtOAc. The organic layers were combined, dried ($MgSO_4$) and filtered. The solvent was removed under vacuum to leave a cream solid. Both products were combined (after comparison by TLC) and recrystallised from methanol (0.08 g, 0.33 mmol, 47%), m.p. 288–290° C.

EXAMPLE 4

8-Hydroxy-3-N-methyl-2-methylquinazolin-4-[3 H]-one (a) 1st Stage—Preparation of 8-Methoxy-3-N-methyl-2-methylquinazolin-4-[3 H]-one 8-Methoxy-2-methylquinazolin-4-[3 H]-one (0.5 g, 2.6 mmol) prepared from 3-methoxy-2-aminobenzamide as previously described was added to dry acetonitrile (60 ml) with potassium carbonate (0.36 g, 2.6 mmol) and methyl iodide (0.16 ml, 2.6 mmol) and the reaction mixture was refluxed for 34 hours. The solvent was removed under vacuum to leave a cream solid which was resuspended in water and extracted into EtOAc. The organic, layers were combined, dried ($MgSO_4$) and filtered. The solvent was removed under vacuum to leave a pale yellow solid, which was recrystallised from EtOAc/petrol (40/60) (0.3 g, 1.47 mmol, 56%), m.p. 133–136° C.

(b) 2nd and Final Stage—Preparation of 8-Hydroxy-3-N-methyl-2-methylquinazolin-4-[3 H]-one A 1.0 M solution of $BBr_3$ in DCM (2.9 ml, 2.9 mmol) was added to 8-methoxy-3-N-methyl-2-methylquinazolin-4-[3 H]-one (0.2 g, 0.98 mmol) to form a yellow suspension, which was gently refluxed for 48 hours. The solvent was directly distilled from the reaction vessel to leave a yellow/green solid, which was hydrolysed with 10% aq. NaOH solution to give a cream suspension. The suspension was neutralised with 1.0 M aqueous HCl and then extracted into EtOAc. The organic layers were combined, dried ($MgSO_4$) and filtered. The solvent was removed under vacuum to leave a pale brown solid (0.18 g, 0.94 mmol, 96% crude yield). The product (0.16 g) was purified by column chromatography, using DCM:MeOH (98:2) as eluent to give a white solid (0.12 g, 0.56 mmol, 57%).

EXAMPLE 5

8-Hydroxy-2-(4'-nitrophenyl)quinazolin-4-[3 H]-one (a) 1st stage—Preparation of 8-Methoxy-2-(4'-nitrophenyl)quinazolin-4-[3 H]-one 3-Methoxy-2-N-(4'-nitrobenzoyl)aminobenzamide (0.5 g, 1.6 mmol) prepared from 3-methoxy-2-aminobenzamide as previously described was suspended in 10% aq. NaOH solution and stirred at 100° C. for 2 hours. The reaction mixture was neutralised with 1.0 M HCl and an orange precipitate formed, which was collected by filtration. The product (0.1 g) was recrystallised from aq. DMF at 100° C., (0.66 g, 0.2 mmol, 66%), m.p. 306–308° C.

(b) 2nd Stage—Preparation of 8-Hydroxy-2-(4'-nitrophenyl)quinazolin-4-[3 H]-one

8-Methoxy-2-(4'-nitrobenzoyl)quinazolin-4-[3 H]-one (0.2 g, 0.7 mmol) was dissolved in a 1.0 M solution of $BBr_3$ in DCM (3 ml, 3 mmol) and gently refluxed under nitrogen for 48 hours. The alkyl bromide was directly distilled from the reaction mixture, and the remaining brown solid was hydrolysed with 10% NaOH solution, to form a black solution, which was acidified with 20% aqueous HCl and a yellow suspension formed. The reaction mixture was extracted with EtOAc and the organic layers were combined, dried ($MgSO_4$) and filtered. The solvent was removed under vacuum to leave a yellow solid, which was recrystallised from aq. propan-2-ol (0.07 g, 0.25 mmol, 38%), m.p. >318° C.

EXAMPLE 6

8-Hydroxy-2-(4'-aminophenyl)quinazolin-4-[3 H]-one

8-Hydroxy-2-(4'-nitrophenyl)quinazolin-4-[3 H]-one, prepared from 3-methoxy-2-aminobenzamide as in Example 5, (50 mg, 0.18 mmol) was suspended in methanol (20 ml) with palladium-carbon catalyst (20 mg) and the reaction vessel was placed under the atmosphere of hydrogen at ambient temperature and pressure. The reaction mixture changed from a yellow suspension to a clear, colourless solution, whereupon the catalyst was removed by filtration through Celite™. The solvent was removed under vacuum to leave a cream pale brown solid, which was recystallised from aq. methanol (25.7 mg, 0.1 mmol, 57%), m.p. >230° C.

EXAMPLE 7

8-Hydroxy-2-(4'-trifluoromethylphenylquinazolin-4-[3 H]-one (a) 1st Stage—Preparation of 8-Methoxy-2-(4'-trifluoromethylphenyl)quinazolin-4-[3 H]-one 3-Methoxy-2-aminobenzamide (0.2 g, 1.2 mmol was dissolved in dry THF (20 ml) with dry pyridine (0.13 ml, 1.6 mmol). 4-Trifluoromethylbenzoyl chloride (0.2 ml, 1.3 mmol) was dissolved in dry THF (2 ml) and added dropwise, whereupon a white precipitate formed. When TLC showed no starting material present, the solvent was removed under vacuum and the remaining white solid was resuspended in 2% aq. NaOH solution. The reaction mixture was neutralised with 1.0 M HCl and the resulting white precipitate was collected by filtration and recrystallised from aq. methanol (0.25 g, 0.8 mmol, 64%), m.p. 287–289° C.

(b) 2nd and Final Stage—Preparation of 8-Hydroxy-2-(4'-trifluoromethylphenyl)quinazolin-4-[3 H]-one 8-Methoxy-2-(4'-trifluoromethylphenyl)quinazolin-4-[3 H]-one (0.1 g, 0.3 mmol) was dissolved in a 1.0 M solution of $BBr_3$ in DCM (9.4 ml, 9.4 mmol) and gently refluxed under nitrogen for 12 hours. The solvent was directly distilled from the reaction mixture to leave a green-yellow solid which was hydrolysed with 10% aq. NaOH solution. The solution was then acidified with 20% aqueous HCl and extracted with EtOAc. The organic layers were combined, dried ($MgSO_4$), filtered and the solvent was removed under vacuum to leave a cream/yellow solid which was collected and dried. The product (51.8 mg) was purified by column chromatography, using EtOAc:petrol 40/60 (4:6) (17.7 mg, 0.06 mmol, 19%).

EXAMPLE 8

8-Hydroxy-2-phenyliquinazolin-4-[3 H]-one 8-methoxy-2-phenylquinazolin-4-[3 H]-one (0.3 g, 1.19 mmol) was suspended in a 1.0 M solution of $BBr_3$ in DCM (3 ml, 3 mmol), under anhydrous conditions, and gently refluxed until the reaction was complete (up to 48 hours). The alkyl bromide was directly distilled from the reaction vessel and the remaining solid residue was cautiously hydrolysed with 10% aq. NaOH solution. The reaction mixture was then neutralised with dilute aqueous HCl. The reaction mixture (or filtrate) was extracted three times into EtOAc. The organic layers were combined, dried ($MgSO_4$), filtered and the solvent was removed under vacuum. The product was purified by recrystallisation from propan-2-ol (0.19 g, 0.75 mmol, 67% yield), m.p. 280–284° C.; Found C 69.54, H 4.05, N 11.46, $C_{14}H_{10}N_2O_2$. 0.1 mol. $H_2O$ requires C 70.05, H 4.28, N 11.67%.

EXAMPLE 9

8-Methyl-2-(4'-hydroxyphenyl)quinazolin-4-[3 H]-one (a) 1st Stage—Preparation of 3-Methyl-2-nitrobenzamide 3-methyl-2-nitrobenzoic acid (2.0 g, 11.0 mmol) was dissolved in dry tetrahydrofuran (THF) under an atmosphere of nitrogen. Thionyl chloride (1.5 equivalent) was added with 2 drops of anhydrous dimethylformamide (DMF) and the reaction mixture was stirred, at room temperature, until TLC indicated the absence of starting material (10–12 hours). The reaction mixture was added dropwise to a stirred solution of aqueous ammonia (6 ml/1 g starting material) and a precipitate formed. After at least 15 minutes, the solvent was removed under vacuum and the remaining slurry was washed with ice-cold water and collected by filtration. The products were used for subsequent reaction without further purification.

(b) 2nd Stage—Preparation of 3-Methyl-2-aminobenzamide

3-Methyl-2-nitrobenzamide (1.20 g, 6.7 mmol) was dissolved in methanol and 10% activated palladium on carbon catalyst (150 mg) was added. The reaction vessel was placed under an atmosphere of hydrogen, at ambient temperature and pressure, until no further hydrogen absorption was observed. The catalyst was removed by filtration of the reaction mixture through a pad of Celite™, which was pre-washed with methanol (150 ml). The solvent was removed under vacuum to give the required product in good yield. The product was used for subsequent reactions without further purification. Yield (0.97 g, 6.4 mmol, 97%), m.p. 145–147° C.

(c) 3rd Stage—Preparation of 8-Methyl-2-(4'-methoxyplenyl)quinazolin-4-[3 H]-one 3-Methyl-2-aminobenzamide (0.2 g, 1.3 mmol) and dry pyridine (1.3 equivalent) were dissolved in dry THF, under an atmosphere of nitrogen. 4-methoxybenzoyl chloride (0.22 ml, 1.5 mmol), in the presence of dimethylaminopyridine (8.1 mg, 5 mol %) was dissolved in dry THF (2 ml) and added dropwise to the reaction mixture, which was stirred at room temperature until TLC indicated the absence of starting material. The solvent was removed under vacuum and the remaining solid was resuspended in 10% NaOH solution and gently refluxed (12 hours) The reaction mixture was neutralised with dilute HCl and the resulting precipitate was collected by filtration. The product was purified by recrystallisation from methanol/water (0.21 g, 0.8 mmol, 58%), m.p. 227–229° C.; Found C 71.89, H 5.23, N 10.20, $C_{16}H_{14}N_2O_2$ requires C 72.17, H 5.30, N 10.52%.

(d) 4th and Final Stage—8-Methyl-2-(4'-hydroxyphenyl) quinazolin-4-[3 H]-one 8-methyl-2-(4'-methoxyphenyl)quinazolin-4-[3 H]-one (0.2 g, 0.7 mmol) was suspended in a 1.0 M solution of $BBr_3$ in DCM (2.3 ml, 2.3 mmol) under anhydrous conditions and was gently refluxed for 48 hours. The alkyl bromide was directly distilled from the reaction vessel and the remaining solid residue was cautiously hydrolysed with 10% aq. NaOH solution. The reaction mixture was then neutralised with dilute HCl In some cases, the resulting precipitate could be collected directly by filtration. The reaction mixture (or filtrate) was extracted three times into EtOAc. The organic layers were combined, dried ($Na_2SO_4$ or $MgSO_4$), filtered and the solvent was removed under vacuum. Product was recrystallised from methanol/water (0.14 g, 0.57 mmol, 76%), m.p. 258–261° C.; Found C 71.34, H 4.86, N 10.82, $C_{15}H_{12}N_2O_2$ requires C 71.41, H 4.79, N 11.11%.

Summary

The present invention should be regarded overall as comprising each and every novel feature or combination of features disclosed herein, and in particular it embraces all the various quinazolinone compounds and intermediates disclosed herein insofar as these are new chemical entities and insofar as these are useful new therapeutic agents, especially by virtue of possessing or providing PARP inhibitory activity. In summary the main aspects of the invention comprise, principally but not exclusively, broadly the following:

(i) Novel compounds of formula (I) as defined herein;
(ii) Compounds of formula (I) with substituents as hereinbefore defined especially for use as prodrugs in carrying out medical treatment, and for use in the manufacture of medical preparations, useful for example as PARP inhibitors to be administered in conjunction with cytotoxic drugs or with radiotherapy to potentiate the effectiveness of the latter in treatment of cancer;
(iii) Processes for the preparation of novel compounds of formula (I) as defined herein, including all novel intermediate compounds produced in carrying out such processes;
(iv) Pharmaceutical formulations comprising a compound of formula (I) as defined herein together with a pharmaceutically acceptable carrier therein; and
(v) Processes for the preparation of a pharmaceutical formulation as defined in (iv) above, e.g. by methods referred to herein.

What is claimed is:

1. A compound having the general structural formula I

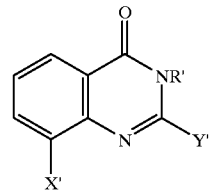

or a pharmaceutically acceptable salt thereof,
wherein
X' represents hydroxyl, alkyl, alkoxy, or O—Z where Z is a phosphate group;
Y' represents hydrogen, alkyl or an optionally substituted aryl group or optionally substituted aralkyl group; and
R' is hydrogen, alkyl, or $CH_2$—O—Z where Z is again a phosphate group;
subject to the proviso that if neither X' nor R' contains Z, Y' is an aryl or aralkyl group having an O—Z substituent therein with Z once again being a phosphate group as hereinabove defined.

2. A compound as claimed in claim 1 wherein Y' is phenyl or benzyl having at least one substituent in the benzene ring selected from hydroxyl, alkoxy, $NO_2$, $N_3$, $NR_5R_6$ ($R_5$ and $R_6$ each being independently hydrogen or alkyl), $NHCOR_3$ ($R_3$ being alkyl or aryl), $CO_2R_4$ ($R_4$ being H or alkyl), an amide $CONR_8R_9$ ($R_8$ and $R_9$ each being independently hydrogen or alkyl), tetrazoyl, alkyl, hydroxyalkyl or a phosphorylated hydroxyalkyl, $CW_3$ or W (W being halogen), CN, and O—Z wherein Z is a phosphate group.

3. A compound as claimed in claim 1 wherein Y' represents a substituted phenyl group having the structural formula II

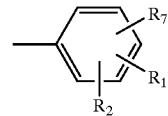

with $R_1$, $R_2$ and $R_7$ each being selected independently from H, hydroxy, alkoxy, $NO_2$, $N_3$, $NR_5R_6$ ($R_5$ and $R_6$ each being independently hydrogen or alkyl), $NHCOR_3$ ($R_3$ being alkyl or aryl), $CO_2R_4$ ($R_4$ being H or alkyl), an amide $CONR_8R_9$ ($R_8$ and $R_9$ each being independently hydrogen or alkyl), tetrazoyl, alkyl, hydroxyalkyl or a phosphorylated hydroxyalkyl, $CW_3$ or W (W being halogen), CN, and O—Z wherein Z is a phosphate group.

4. A compound as claimed in claim 3 wherein one of the substituents $R_1$, $R_2$ and $R_7$ is 4-CN, 4-$CO_2H$, 4-tetrazole or is 3-$OPO_3^{--}$ or 4-$OPO_3^{--}$ wherein, when one of said substituents $R_1$, $R_2$ and $R_7$ is 3-$OPO_3^{---}$ or 4-$OPO_3^{---}$ the compound is in the form of a pharmaceutically acceptable salt while the remainder of these substituents $R_1$, $R_2$ and $R_7$ are each hydrogen.

5. A compound as claimed in claim 1 wherein substituents X' and Y' at the 8 and 2 positions of the quinazolinone molecule both include a phosphate group.

6. A compound as claimed in claim 1 wherein O—Z represents a monobenzyl phosphate diester.

7. A compound as claimed in claim 1 wherein the alkyl group present, either as such or as a moiety in another group, contains 1–6 carbon atoms.

8. A compound as claimed in claim 1 wherein X' or Y' is, or includes, an alkyl group which is a $C_{1-4}$ alkyl group.

9. A compound as claimed in claim 1 wherein R' is methyl.

10. The compound 8-(O-phosphoryl)-2-methylquinazolin-4-[3 H]-one or a pharmaceutically acceptable salt thereof.

11. A compound as claimed in claim 1 which is in the form of a water-soluble ammonium or alkali metal phosphate salt.

12. A process for preparing a compound as claimed in claim 1 comprising treating a corresponding hydroxy quinazolinone compound with a phosphorylating agent to convert the hydroxyl thereof into a dibenzyl phosphate ester grouping, followed by a subsequent stage of selectively removing one or both of the benzyl groups.

13. A process as claimed in claim 12 wherein the phosphorylation reaction is carried out using dibenzyl chlorophosphonate as the phosphorylating agent in the presence of a base.

14. A process for preparing a compound as claimed in claim 1 wherein a quinazolinone compound of structural formula III

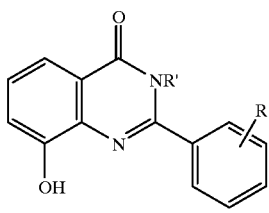

III wherein R is selected from 4'-CN, 4'-$NH_2$, 4'-$CO_2Me$, 4'-COOH; 4-OH, 4'-$CF_3$, 4'-$CONH_2$ and 4'-tetrazole, and R' is selected from hydrogen and $C_{1-6}$ alkyl is reacted with a dibenzyl chlorophosphonate.

15. A pharmaceutical composition comprising an effective amount of a compound as claimed in claim 1 and a carrier therefor in unit dosage form suitable for administration to a mammal in order to provide PARP-inhibiting treatment in the course of therapy.

16. A pharmaceutical composition for use in conjunction with a cytotoxic drug or radiotherapy in order to increase the cytotoxic effectiveness of the latter in antitumour treatment, said composition comprising an effective PARP-inhibiting amount of a quinazolinone phosphate compound as claimed in claim 1 and a pharmaceutically acceptable carrier therefor.

17. A pharmaceutical composition as claimed in claim 16 in the form of a sterile liquid preparation for parental use comprising a predetermined therapeutically effective non-toxic amount of said quinazolinone phosphate compound dissolved in buffered saline and in unit dosage form in sealed ampoules ready for use.

18. A method of therapeutic treatment carried out on a mammal to bring about a beneficial inhibition of activity of PARP enzyme, said method comprising administering to said mammal an effective PARP-inhibiting amount of a compound as claimed in claim 1.

19. A method as claimed in claim 18 carried out in conjunction with administration of a DNA-damaging cytotoxic drug or radiotherapy in the course of antitumour therapy.

* * * * *